US011678430B2

(12) United States Patent
Jauregui et al.

(10) Patent No.: US 11,678,430 B2
(45) Date of Patent: Jun. 13, 2023

(54) NEUTRON GENERATING TARGET FOR NEUTRON BEAM SYSTEMS

(71) Applicant: TAE TECHNOLOGIES, INC., Foothill Ranch, CA (US)

(72) Inventors: Frank Jauregui, Fountain Valley, CA (US); Michael Meekins, Silverado, CA (US); Swati Bhanderi, River Vale, NJ (US); Anatoly B. Muchnikov, Mission Viejo, CA (US)

(73) Assignee: TAE TECHNOLOGIES, INC., Foothill Ranch, CA (US)

( * ) Notice: Subject to any disclaimer, the term of this patent is extended or adjusted under 35 U.S.C. 154(b) by 0 days.

(21) Appl. No.: 17/004,742

(22) Filed: Aug. 27, 2020

(65) Prior Publication Data

US 2021/0076481 A1 Mar. 11, 2021

Related U.S. Application Data

(60) Provisional application No. 62/894,106, filed on Aug. 30, 2019.

(51) Int. Cl.
*H05H 6/00* (2006.01)
*H05H 3/06* (2006.01)
(Continued)

(52) U.S. Cl.
CPC ............ *H05H 3/06* (2013.01); *A61N 5/10* (2013.01); *G21G 4/02* (2013.01); *H05H 6/00* (2013.01)

(58) Field of Classification Search
CPC .. G21G 1/10; G21G 4/02; H05H 3/06; H05H 6/00; G21K 5/08
See application file for complete search history.

(56) References Cited

U.S. PATENT DOCUMENTS

| 2,935,633 | A | * | 5/1960 | Peters | ..................... | H05H 6/00 |
| | | | | | | 376/115 |
| 3,860,827 | A | * | 1/1975 | Granberg | ................. | H05H 6/00 |
| | | | | | | 376/151 |

(Continued)

FOREIGN PATENT DOCUMENTS

| CN | 207856090 U | 9/2018 |
| CN | 109381802 A | 2/2019 |

(Continued)

OTHER PUBLICATIONS

Blue, T. E., et al., "Accelerator-based epithermal neutron sources for boron neutron capture therapy of brain tumors", Journal of Neuro-Oncology, 2003, vol. 62, pp. 19-31.

(Continued)

*Primary Examiner* — Sharon M Davis
(74) *Attorney, Agent, or Firm* — Alston & Bird LLP

(57) ABSTRACT

Embodiments that are directed to a target for producing a high epithermal neutron yield for boron-neutron capture therapy (BNCT) treatments are disclosed. The target includes a thin flat film of solid lithium mounted onto a heat-removal support structure that is cooled with a liquid coolant and configured to maintain the turbulent flow regime for a liquid coolant and distribute the flow of coolant directed at the center of the support structure toward a periphery of the support structure via a plurality of channels formed in the support structure. The support structure includes a nozzle located at its center to direct coolant flow outwardly from the center to avoid stagnant water flow at the center of the support structure. Systems, device, and methods utilizing the approaches are also described.

10 Claims, 7 Drawing Sheets

(51) Int. Cl.
*A61N 5/10* (2006.01)
*G21G 4/02* (2006.01)

(56) References Cited

U.S. PATENT DOCUMENTS

| | | | | |
|---|---|---|---|---|
| 4,812,775 | A * | 3/1989 | Klinkowstein | A61N 5/10 250/299 |
| 2006/0140326 | A1 * | 6/2006 | Rowland | H05H 3/06 376/114 |
| 2007/0297554 | A1 * | 12/2007 | Lavie | G21G 1/10 376/190 |
| 2010/0067640 | A1 | 3/2010 | Willis et al. | |
| 2016/0270202 | A1 * | 9/2016 | Shioda | H05H 6/00 |
| 2017/0062086 | A1 | 3/2017 | Park, Jr. et al. | |
| 2019/0148102 | A1 * | 5/2019 | Maltz | H01J 35/18 378/130 |

FOREIGN PATENT DOCUMENTS

| | | | | |
|---|---|---|---|---|
| EP | 1895819 A1 * | 3/2008 | | H05H 6/00 |
| RU | 2 282 908 C2 | 8/2006 | | |
| WO | WO 2014/039579 A2 | 3/2014 | | |
| WO | WO 2019/029483 A1 | 2/2019 | | |

OTHER PUBLICATIONS

Stupp, R., et al., "Radiotherapy plus Concomitant and Adjuvant Temozolomide for Glioblastoma", N Engl J Med, 2005, vol. 352, No. 10, pp. 987-996.

Yamamoto, T., et al., "Boron neutron capture therapy for newly diagnosed glioblastoma", Radiotherapy and Oncology, 2009, vol. 91, No. 1, pp. 80-84.

Sauerein, et al., "Neutron Capture Therapy, Principles and Applications," Springer, DOI 10.1007/978-3-642-31334-9, (eBook) (2012).

Badrutdinov, et al., "In Situ Observations of Blistering of a Metal Irradiated with 2-MeV Protons," Metals, 7, 558; doi:10.3390/met7120558, (Dec. 2017).

Lyublinski, et al., "Stationary operated lithium in-vessel elements of a tokamak," DOI: 10.21517/0202-3822-2020-43-1-55-63, Article, (Apr. 2020).

Taskaev, "Development of an Accelerator-Based Epithermal Neutron Source for Boron Neutron Capture Therapy," Physics of Particles and Nuclei, vol. 50, No. 5, pp. 569-575, (Mar. 2019).

Taskaev, "Accelerator Based Epithermal Neutron Source," Physics of Particles and Nuclei, vol. 46, No. 6, pp. 956-990, (Nov. 2015).

Yoshioka, "Review of Accelerator-Based Boron Neutron Capture Therapy Machines," Proceedings of IPAC2016, Busan, Korea, May 12, 2016, THXB01, ISBN 978-3-95450-147-2, pp. 3171-3175.

Kiyanagi, "Accelerator-based neutron source for boron neutron capture therapy," Review Article, Ther Radiol Oncol, 2:55, (Nov. 2018).

Bayanov, et al., "Lithium neutron producing target for BINP accelerator-based neutron source," Applied Radiation and Isotopes, 61, pp. 817-821, (Nov. 2004).

\* cited by examiner

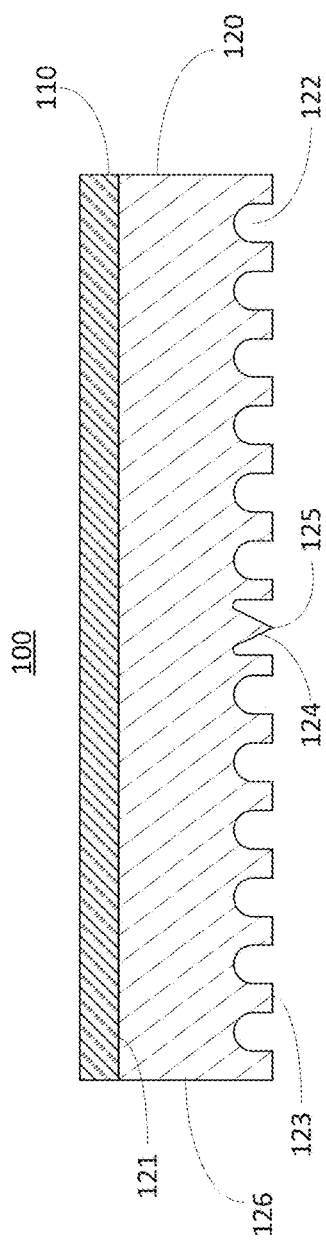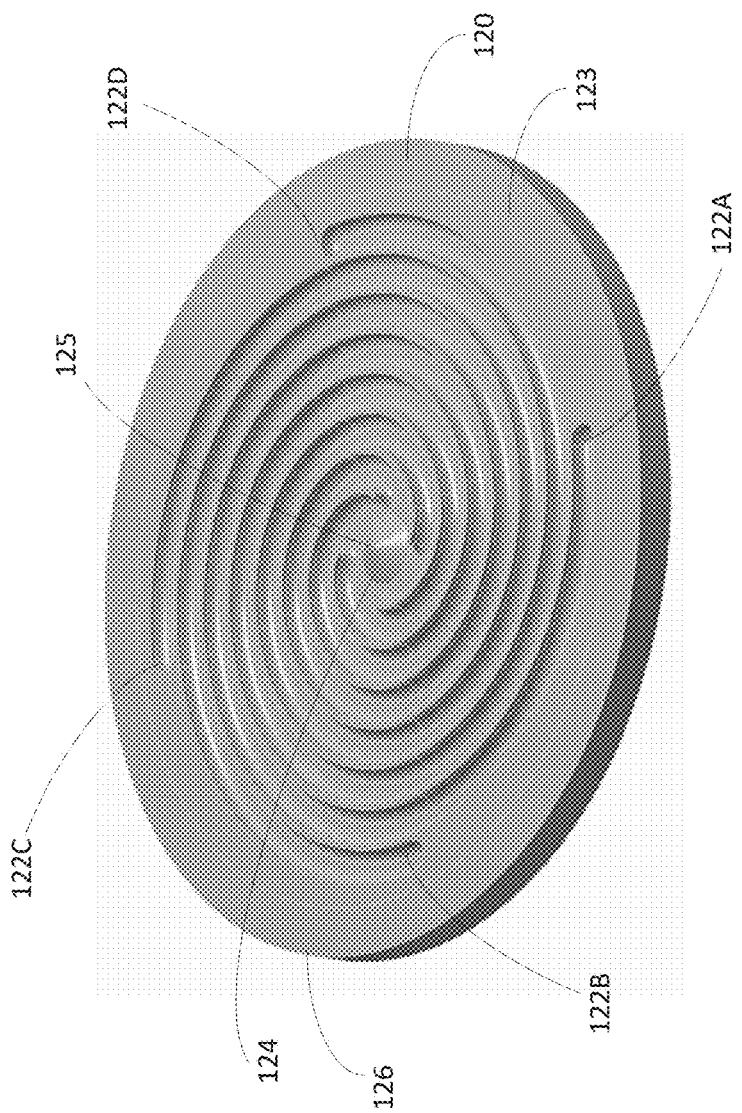

NEUTRON GENERATING TARGET FOR NEUTRON BEAM SYSTEMS

CROSS-REFERENCE TO RELATED APPLICATIONS

This application claims the benefit of and priority to U.S. provisional patent application Ser. No. 62/894,106, filed Aug. 30, 2019, which is incorporated by reference herein in its entirety for all purposes.

FIELD

The subject matter described herein relates generally to neutron beam systems and, in particular, to a neutron generating target, and, further in particular, systems and methods for facilitating the generation of neutrons for neutron beam systems.

BACKGROUND

Boron neutron capture therapy (BNCT) is a cancer radiation therapy, which appears promising especially for some of the toughest cancers. Studies appear to show that BNCT treatment results in greater survival time as compared to treatments utilizing other therapies such as, e.g., X-Ray therapy [see, e.g., Yamamoto et al., Radiation Therapy and Oncology 2009; Stupp et al., Lancet 2009]. To date, the majority of BNCT treatment procedures are performed at nuclear reactors from which demanded epithermal neutron beams can be procured.

However, it is obvious that for clinical treatments the use of nuclear reactors would not be appropriate. Recently proposed alternative method for producing epithermal neutron beams include accelerator based solutions [see, e.g., Blue T., Yanch J. Accelerator-based epithermal neutron sources for boron neutron capture therapy of brain tumors. Neuro-Oncol. 2003. V.62. P. 19-31].

Currently, the most effective way of generating epithermal neutrons appears to utilize the 7Li(p, n)7Be nuclear reaction (~1.88 megaelectron-volts (MeV) threshold). The intensity of neutrons requirement and other factors tend to dictate the "consensus" neutron source rate for a clinical application of about $10^{13}$ neutrons per second (n/s) from a lithium target. This "consensus" neutron source rate value tends to dictate performance requirements of a proton beam, which interacts with the lithium target, corresponding to a beam energy of about 2-2.5 MeV and a beam current of about 10-15 mA, with a heat load of the target on the order of about 20-30 kilowatts (kW).

For lithium metal, which has a relatively low melting point (about 180 degrees Celsius (° C.)) and poor thermal conductivity, a major obstacle in the design of a lithium target is the ability to dissipate a high heat load while, at the same time, maintaining the lithium in its solid state. The requirement of solid lithium is due to extremely high toxicity and radioactivity of the 7Be—the byproduct of 7Li(p, n)7Be reaction.

Conventional solutions tend to be complicated and tend to provide less than optimal cooling. RU 2282908 discusses a neutron-producing target assembly that has a target with active material consisting essentially of a thin-walled shell of revolution made in the form of sphere or cylinder and disposed within a casing filled with circulating cooling medium. Assembly requires a means for setting the target in rotary motion and a means for limiting cooling medium ingress to an inlet window space. U.S. Publ. No. 2010/0067640A1 utilizes a target system configured with a geometry comprising a conical shape substrate with the lithium deposited onto the substrate. The proposed geometry is intended to increase target cooling by providing an increased surface area.

For these and other reasons, needs exist for improved systems, devices, and methods that facilitates a high heat-load lithium target for neutron generation.

SUMMARY

Example embodiments of systems, devices, and methods are described herein for accelerator based neutron sources, and, more particularly, systems and methods for facilitating neutron generation for neutron beam systems. For practical implementation of boron-neutron capture therapy (BNCT) treatments, a high epithermal neutron yield of greater than about $10^{13}$ n/s is preferred. In example embodiments, a target for producing a high epithermal neutron yield preferably includes a thin flat film of solid lithium mounted onto a heat-removal support structure. The heat-removal support structure is preferably directly cooled with a liquid coolant. The thermal management of the support structure is configured to accommodate an extremely high heat flux. The heat-removal support structure's ability to accommodate an extremely high heat flux enables a neutron beam system utilizing a target with such support structure to use a high current proton beam having high beam energies and currents. In certain example embodiments, the support structure is configured to accommodate an extremely high heat flux of up to about 3-4 megawatts per square meter ($MW/m^2$), which enables the neutron beam system to utilize a high current proton beam with the energy of about 2-2.5 MeV and beam current up to about 10 milliamps (mA) (i.e., a total beam power up to about 25 kW).

The heat-removal support structure is preferably configured to maintain the turbulent flow regime for a liquid coolant. For the forced convection cooling (which is the case for our situation), the most effective flow is a turbulent one. The intense mixing of the coolant in the turbulent flow promotes the heat and the momentum transfer between fluid particles, thus significantly enhancing the thermal conductivity.

In example embodiments, the heat-removal support structure is configured to distribute the flow of water directed at the center of the support structure toward the periphery of the support structure via a plurality of channels formed in a side or surface of the support structure. The number of channels formed in the support structure depends on the specific realization and preferably is an even number, starting at two (2) through n, for the symmetry of the design. The plurality of channels extending from a position proximate the center of the support structure towards the periphery of the support structure. The plurality of channels form a configuration of parallel spiral windings to evenly distribute cooling across a maximum area of the substrate structure.

The support structure includes a nozzle located at the center of the side of the support structure. The nozzle directs the water flow outwardly from the center to avoid stagnant water flow at the center of the support structure, which potentially can cause a hotspot in the center of the support structure. Thus, the nozzle facilitates more uniform temperature distribution on the beam (or upstream) side of the target. The nozzle is further configured to provide a minimum pressure drop for the inlet water, thus directing the water flow from one direction to another, i.e., rotating it by 90°, and minimizing the resistance on the water flow. The size of the nozzle as well as its geometry is optimized to maintain the turbulent regime of the flow and at the same time to avoid stagnant eddies. The nozzle is one of conically shaped or semi-spherically shaped.

In example embodiments, a neutron beam system includes a low energy beamline serving as an ion beam injector, a high voltage (HV) tandem accelerator coupled to the ion beam injector, and a high-energy beamline extending from the tandem accelerator to a neutron target assembly housing a neutron-producing target. In example embodiments, the ion beam injector includes an ion source, beam optics incorporated into a low-energy ion source vacuum box extending from the ion source, a pre-accelerator coupled to the low-energy ion source vacuum box, beam diagnostics and a pumping chamber coupled to the tandem accelerator. The ion source generates charged particles in the plasma volume which can be extracted, accelerated, conditioned and eventually used to produce neutrons when delivered to the neutron producing target.

Other systems, devices, methods, features and advantages of the subject matter described herein will be or will become apparent to one with skill in the art upon examination of the following figures and detailed description. It is intended that all such additional systems, methods, features and advantages be included within this description, be within the scope of the subject matter described herein, and be protected by the accompanying claims. In no way should the features of the example embodiments be construed as limiting the appended claims, absent express recitation of those features in the claims.

BRIEF DESCRIPTION OF FIGURES

The details of the subject matter set forth herein, both as to its structure and operation, may be apparent by study of the accompanying figures, in which like reference numerals refer to like parts. The components in the figures are not necessarily to scale, emphasis instead being placed upon illustrating the principles of the subject matter. Moreover, all illustrations are intended to convey concepts, where relative sizes, shapes and other detailed attributes may be illustrated schematically rather than literally or precisely.

FIG. 3 is a cross-sectional view drawing depicting an example embodiment of a neutron-generating target.

FIG. 4 is a perspective view drawing of a support structure of the neutron-generating target shown in FIGS. 3, 5, 6 and 7.

DETAILED DESCRIPTION

Figure 1:
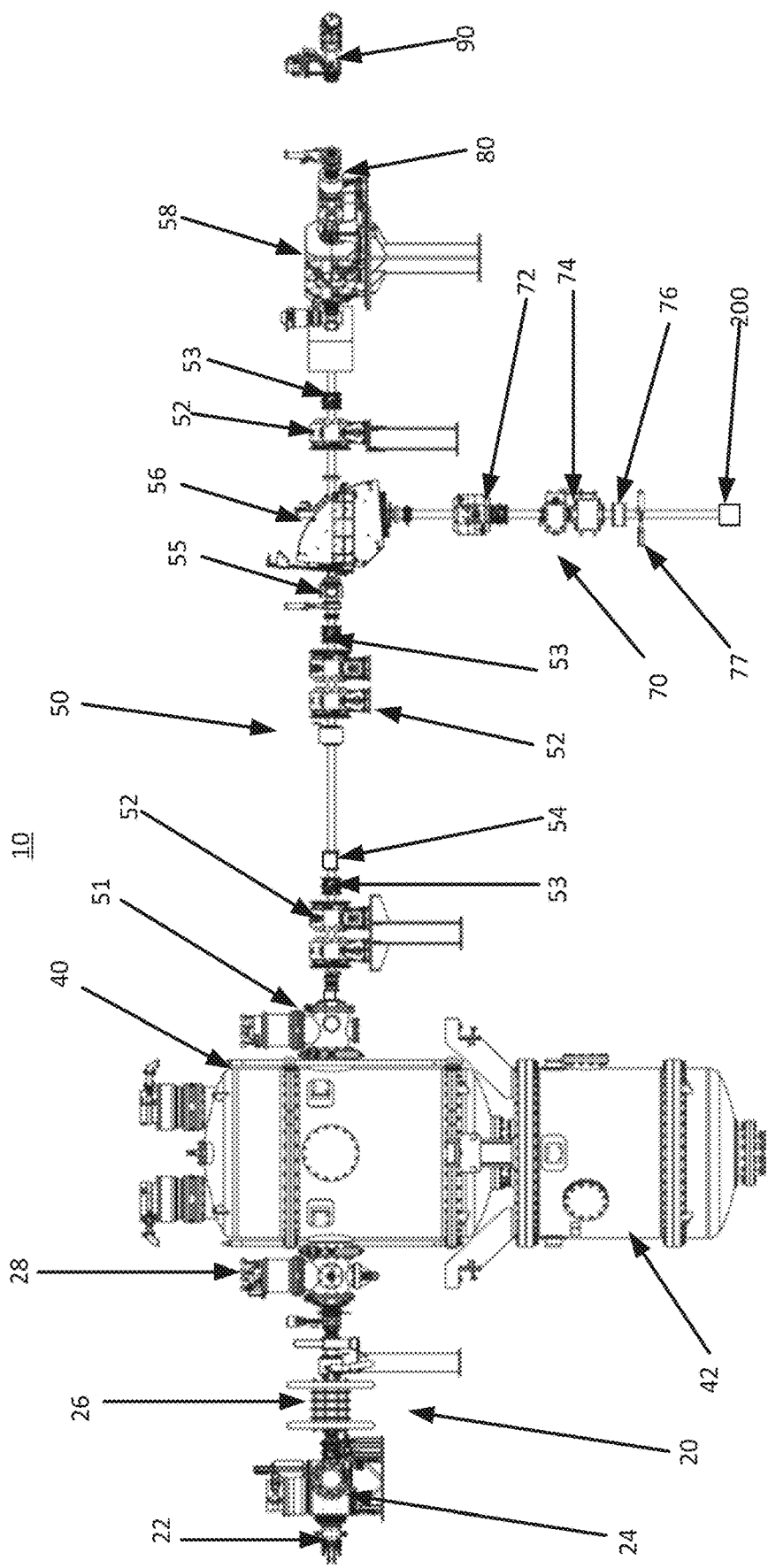
FIG. 1 is a front view drawing depicting an example embodiment of a neutron beam system.

Before the present subject matter is described in detail, it is to be understood that this disclosure is not limited to the particular embodiments described, as such may, of course, vary. It is also to be understood that the terminology used herein is for the purpose of describing particular embodiments only, and is not intended to be limiting, since the scope of the present disclosure will be limited only by the appended claims.

Example embodiments of systems, devices, and methods are described herein for a neutron beam source, and, more particularly, systems and methods for facilitating neutron generation for neutron beam systems. For practical implementation of boron-neutron capture therapy (BNCT) treatments, a high epithermal neutron yield of greater than about $10^{13}$ n/s is preferred. In example embodiments, a target for producing a high epithermal neutron yield preferably includes a thin flat film of solid lithium mounted onto a heat-removal support structure. The heat-removal support structure is preferably directly cooled with a liquid coolant. The thermal management of the support structure is configured to accommodate an extremely high heat flux. The support structure's ability to accommodate an extremely high heat flux enables a neutron beam system utilizing a target with such support structure to use a high current proton beam having high beam energies and currents. In certain example embodiments, the support structure is configured to accommodate an extremely high heat flux of up to about 3-4 $MW/m^2$, which enables the neutron beam system to utilize a high current proton beam with the energy of about 2-2.5 MeV and beam current up to about 10 mA (i.e., a total beam power up to about 25 kW).

The heat-removal support structure is preferably configured to maintain the turbulent flow regime for a liquid coolant. For forced convection cooling, the most effective flow is a turbulent one. The intense mixing of the coolant in the turbulent flow promotes the heat and the momentum transfer between fluid particles, thus significantly enhancing the thermal conductivity.

In example embodiments, a neutron-generating target configuration provides effective cooling of the target with room temperature water. For example, using water with a temperature of about 25° C. and a flow rate of about 2.16 cubic meters per hour effectively cools a target having a maximum target temperature (on a beam side of the target) of less than about 145° C. at a heat load of about 25 kW.

In example embodiments, a neutron-generating target includes a protection layer that covers a lithium layer. The interaction of lithium with other elements can destroy the lithium layer of the target. For example, interaction of lithium with nitrogen results in the formation of a nitride, which peels off the surface of the lithium layer, destroying the lithium layer. Similarly, the interaction of lithium with oxygen results in the formation of an oxide, which peels off the surface of the lithium layer, destroying the lithium layer. The protective layer could be made of different materials, preferably low Z materials like carbon. The protective layer exhibits good adhesion to lithium, thus protecting the lithium layer from direct contact with atmospheric air. This feature facilitates simplified transport of the lithium target from the deposition facility directly to a treatment facility such as a hospital or lab where the neutron beam system is located. The protective layer on the target surface tends to advantageously eliminate the need for special transportation devices having an inert gas atmosphere inside.

In example embodiments, a neutron beam system includes a low energy beamline serving as an ion beam injector, a high voltage (HV) tandem accelerator coupled to the ion beam injector, and a high-energy beamline extending from the tandem accelerator to a neutron target assembly housing a neutron-producing target. In example embodiments, the ion beam injector includes an ion source, beam optics incorporated into a low-energy ion source vacuum box extending from the ion source, a pre-accelerator coupled to the low-energy ion source vacuum box, and a pumping chamber (with a built-in Faraday cup) coupled to the pre-accelerator and the tandem accelerator. The ion source serves as a reliable source of charged particles which can be accelerated, conditioned and eventually used to produce neutrons when delivered to the neutron producing target.

Figure 2:
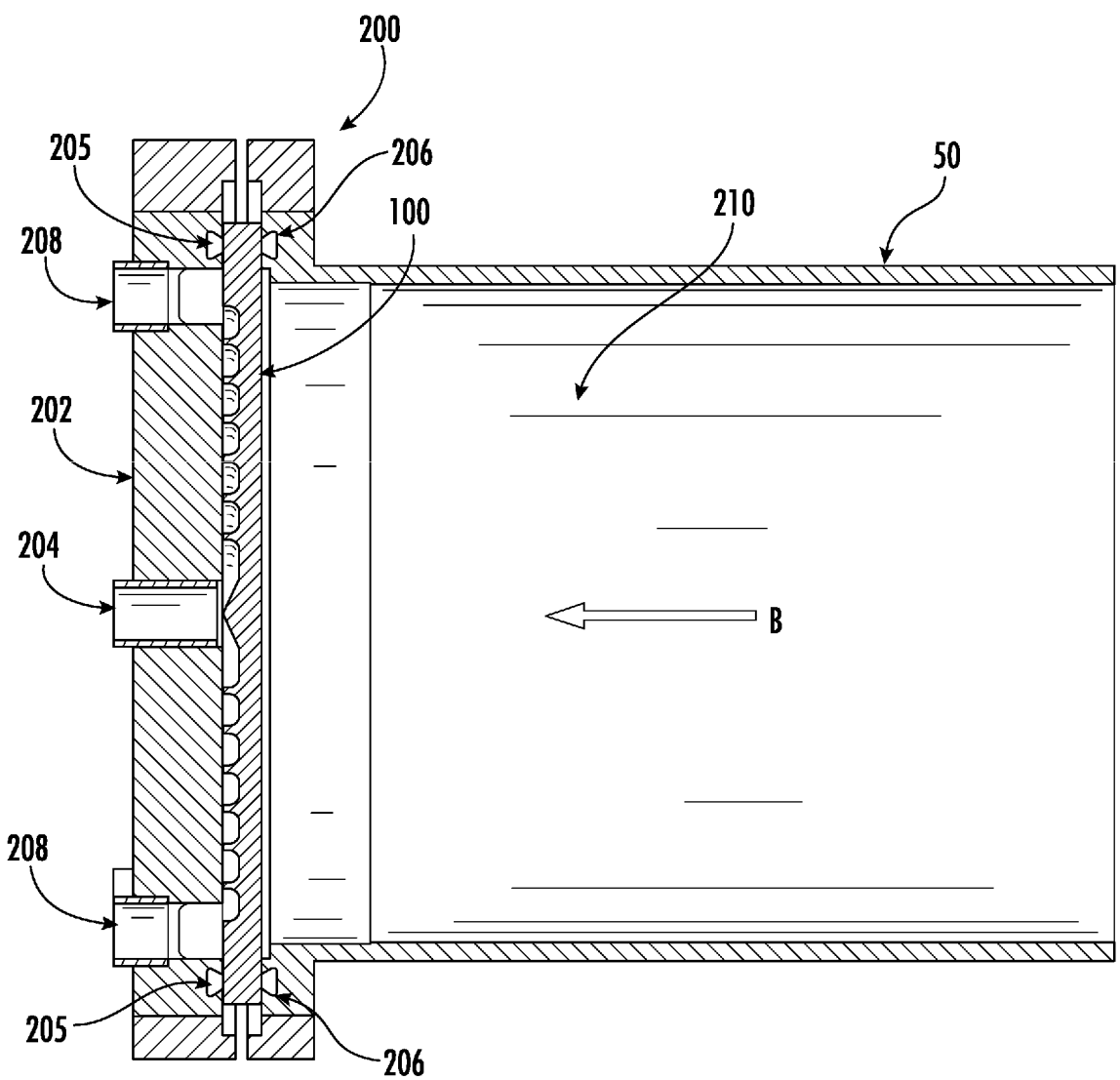
FIG. 2 is a cross-sectional view drawing depicting an example embodiment of a target assembly subsystem of the neutron beam system shown in FIG. 1

Turning in detail to the figures, FIG. 1 shows an example embodiment of an accelerator based neutron beam system 10. The neutron beam system 10 includes a low energy beam line serving as an ion beam injector 20 (as shown in FIG. 2), a high voltage (HV) tandem accelerator 40 coupled to the ion beam injector 20, and a high-energy beamline 50 extending from the tandem accelerator 40 to a neutron target assembly 200 housing a neutron-producing target. The ion beam injector 20 includes an ion source 22, an ion source vacuum box 24, which is low energy, extending from the ion source 22, a pre-accelerator 26 coupled to the low-energy ion source vacuum box 24 and a pumping chamber (with a built-in Faraday cup) 28 coupled to the pre-accelerator 26 and the tandem accelerator 40. The ion source 22 serves as a source of charged particles (which in example embodiments are negative hydrogen ions) which can be accelerated, conditioned and eventually used to produce neutrons when delivered to a neutron producing target.

There are two types of negative ion sources 22, which differ by the mechanism of generation of negative ions: the surface type and volume type. The surface type requires presence of cesium (Cs) on the specific internal surfaces. A discussion of a surface type negative ion source is provided in published PCT Publication No. 2014/039579 A2, which is incorporated herein by reference. The volume type relies on formation of negative ions in the volume of a high current discharge plasma. Both types of ion sources can deliver the required negative ion current.

The ion source vacuum box 24, pre-accelerator 26 and pumping chamber 28, which form a low energy beamline extending from the ion source 22 to the tandem accelerator, are configured to transfer the ion beam from the ion source 22 to the input of the tandem accelerator 40. This low energy beamline may have a few magnetic and electrostatic elements to focus and steer the beam to match the beam to the beamline axis and the acceptance angle of the tandem accelerator 40. The ion source vacuum box 24 may have ion optics positioned therein.

The pre-accelerator 26 provides acceleration of the ion beam injected from the ion source 22. The pre-accelerator 26 serves an important function of beam focusing to achieve overall convergence to match the aperture area at the high voltage tandem accelerator 40.

The tandem accelerator 40, which is powered by a high voltage power supply 42 coupled thereto, produces a proton beam with an energy equal to twice the voltage applied to the accelerating electrodes positioned within the tandem accelerator 40. The energy level of the proton beam is achieved by accelerating the beam of hydrogen ions from the input of the tandem accelerator 40 to the innermost high-potential electrode, stripping two electrons from each ion, and then accelerating the resulting protons downstream by the same applied voltage.

The high-energy beamline 50 is designed to transfer the proton beam from the output of the tandem accelerator 40 to the neutron-generating target in the neutron target assembly 200 positioned at the end of a branch 70 of the beamline extending into patient treatment room. In the example embodiment shown in FIG. 1, the high-energy beamline 50 includes 3 branches 70, 80 and 90 to extend into three (3) different patient treatment rooms. The high-energy beamline 50 includes a pumping chamber 51, quadrupole magnets 52 and 72 to prevent de-focusing of the beam, dipole or bending magnets 56 and 58 to steer the beam into treatment rooms, beam correctors 53, diagnostics such as current monitors 54 and 76, fast beam position monitors section 55, and a scanning magnet 74.

The design of the high-energy beamline 50 depends on the configuration of the treatment facility. The embodiment shown on FIG. 1 implements a two-story configuration of the treatment facility. One of the treatment rooms, which is closer to a target assembly 200 is located on the lower story. The beam is delivered to this target assembly 200 with the use of the bending magnet 56. After that, quadrupole magnets 72 focus the beam to the certain size at the target. Then, the beam enters the scanning magnets 74, which provides rastering of the beam onto the target surface in a special spiral motion manner. The beam rastering achieves smooth and even time-averaged distribution of the proton beam on the lithium target, preventing overheating and making the neutron generation as uniform as possible within the lithium layer. After entering the scanning magnets 74, beam is delivered into a current monitor 76, which measures beam current. The main idea of using the current monitor is safety, since the measured beam current value is included in safety interlock. The target assembly 200 can be physically separated from the high energy beamline volume with a gate valve 77. The main function of the gate valve is separating of the vacuum volume of the beamline from the target while target exchange/loading. The horizontal orientation of the beamline (second and possibly third treatment rooms off branches 80 and 90) is shown (partially) on FIG. 1 as well. In this case the beam is not bent by 90 degrees by a bending magnet 56, it rather goes straight to the right, then it enters the quadrupole magnets 52, which are located in the horizontal beamline. After, the beam could be bent by another bending magnet 58 to a needed angle, depending on the room configuration. Otherwise, the bending magnet 58 could be replaced with a Y-shaped magnet in order to split the beamline into two directions for two different treatment rooms located on the same floor.

A cross-sectional view of an example embodiment of the target assembly 200 is shown in FIG. 2. In the embodiment shown, a neutron-generating target 100 is enclosed in between a cap 202 and a vacuum part 210 of the high energy beamline 50. An arrow B shows the direction of the beam. The cap 202 is bolted to the beamline 50, thus providing a vacuum tight seal 206 in between the target 200 and the vacuum part 210 of the high energy beamline 50, and a water tight seal 205 between the target structure 100 and a cooling water inlet 204 and outlets 208.

Turning to FIGS. 3 and 4, a cross-sectional view of an example embodiment of the neutron-generating target 100 is shown. The neutron-generating target 100 includes a thin lithium layer 110 adhered to a substrate (heat removal) structure 120 on a first (or upstream) side 121 of the substrate 120. A proton beam propagates from the tandem accelerator 40 along the high-energy beam line 50 and interacts with the lithium layer 110, producing neutrons and turning lithium into a radioactive isotope of beryllium, 7Be. The lithium layer 110 preferably has a thickness that enables protons to exit the lithium layer 110 after the proton energy drops below the threshold of the nuclear reaction for neutron formation, 1.89 MeV. Protons preferably leave the lithium layer 110 when their energy drops below 1.89 MeV to prevent further energy deposition in the lithium layer 110, which is inefficient and leads to heating of the lithium layer 110 without neutron production. Protons should penetrate through the lithium layer 110 to the substrate structure 120 and fully dissipate their energy in the substrate structure 120. The substrate structure 120 is made of material having a high thermal conductivity such as, for example, copper, copper-diamond powder composites, CVD diamond, and the like.

A second (or downstream) side 123 of the substrate structure 120 is actively cooled by a water flow, designed to remove the heat power (e.g., about 25 kW heat power). Cooling water enters through a water inlet duct (204, see FIG. 2) at the center 125 of the second side 123 of the substrate structure 120 and flows to the periphery of the substrate structure 120 via a plurality of channels 122 formed in the downstream side 123 of the substrate 120. The number of channels 122 formed in the substrate depends on the specific realization and preferably is an even number, starting at two (2) through n, for the symmetry of the design. The number of the water outlet ducts 208 is also preferably an even number.

The flat layer of lithium 110 advantageously enables the creation of a planar neutron source. A planar neutron source is advantageous in comparison to, for example, a conical shape neutron source (see, e.g., U.S. Publ. No. 2010/0067640 A1), since a planar neutron source tends to simplify simulation and manufacture of a corresponding beam shaping assembly.

Figure 5:
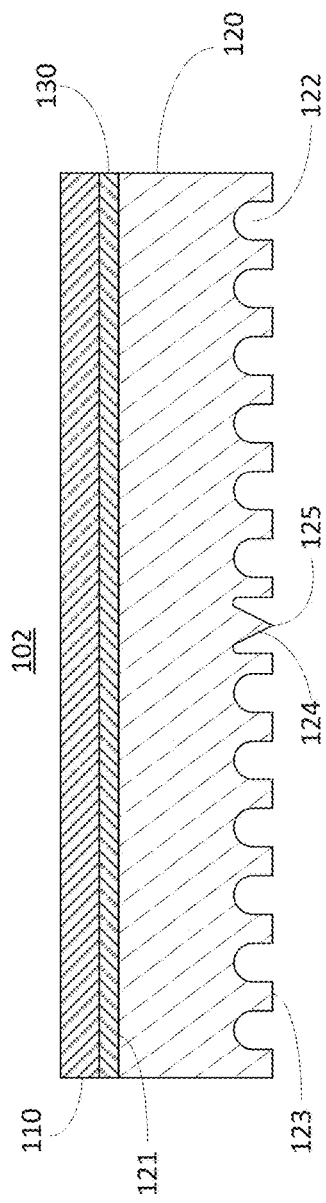
FIG. 5 is a cross-sectional view drawing depicting another example embodiment of a neutron-generating target.

Turning to FIG. 5, an alternative example embodiment of the neutron-generating target 102 is shown to include a thin lithium layer 110 positioned on a first (or upstream) side 121 of a substrate structure 120 with an interlayer 130 interposing the lithium layer 110 and the substrate structure 120. The interlayer 130 is fabricated out of material with high solubility for Hydrogen and/or with high diffusion coefficient for Hydrogen. As a result, the interlayer 130 reduces the blistering phenomena. Formation of blisters (little bubbles of Hydrogen inside the substrate) leads to an increase of surface temperature, which promotes evaporation of the lithium layer 110. The material for the interlayer 130 may be one of the following: pure tantalum (Ta), titanium (Ti), lead (Pd), niobium (Nb), vanadium (V), nickel (Ni), or alloys of these elements with themselves or/and with copper.

Figure 6:
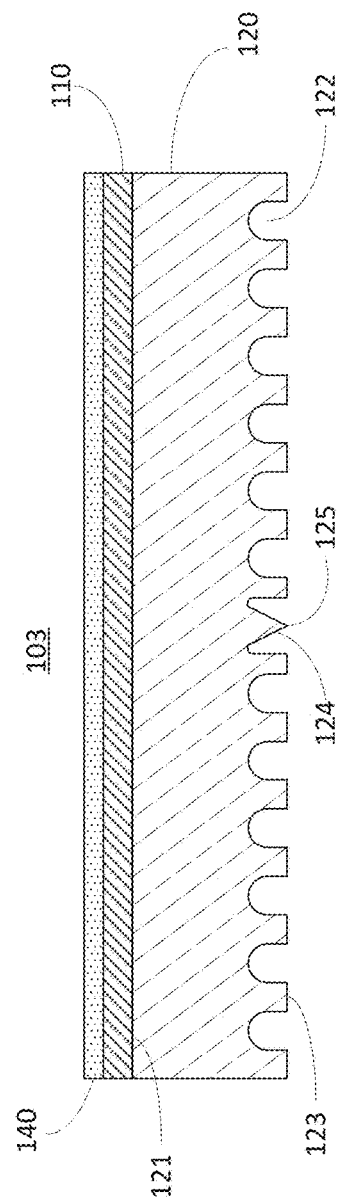
FIG. 6 is a cross-sectional view drawing depicting another example embodiment of a neutron-generating target.
Figure 7:
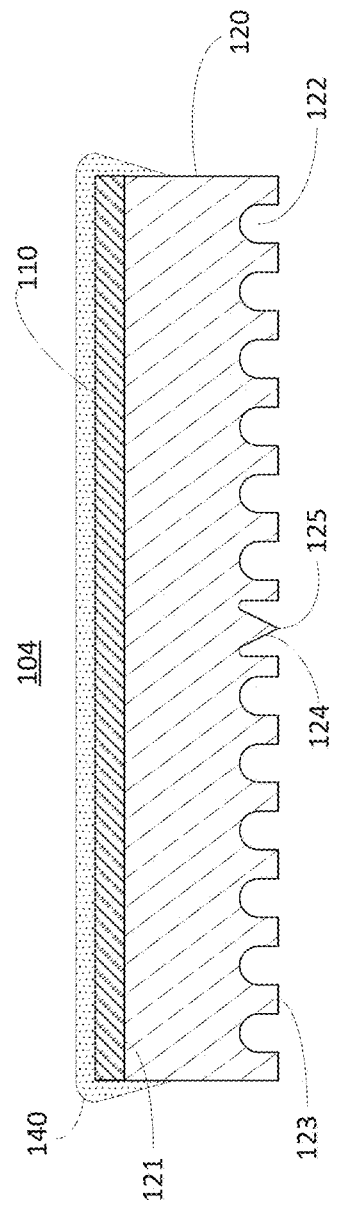
FIG. 7 is a cross-sectional view drawing depicting another example embodiment of a neutron-generating target.

FIG. 6 illustrate another example embodiment of a neutron-generating target 103, which utilizes a special protective layer 140, which is placed on top of the lithium layer 110. The protective layer 140 acts as a shell, which contains the poisonous/radioactive 7Be and prevents dispersion of 7Be outside the target 103. The protective layer 140 also prevents interaction of lithium in the layer 110 with atmospheric air, which leads to oxidation of the lithium and formation of lithium nitride and/or nitrate.

The protective layer 140 could be made of different materials, preferably low Z materials, like carbon, aluminum, and the like. The thickness of the layer 140 preferably does not exceed a predetermined limit to prevent excessive energy loss of the protons of the proton beam. The material of the layer 140 preferably has good adhesion to lithium, preventing the lithium from contact with atmospheric air.

In a slightly modified example embodiment of a neutron-generating target 104 shown in FIG. 6, the protective layer 140 is made of a highly thermal conductive material and is attached to the lithium layer 110 in a manner such that the protective layer 140 covers all of the lithium layer 110 evenly at the top and on the sides of the lithium layer 110. With the lithium layer 110 completely covered, even in a worst-case scenario when the lithium layer 110 is overheated above its melting point, beryllium will not be spread out of the layer 110 due to the protecting layer 140.

Referring back to FIGS. 3 and 4, the substrate structure 120 includes a nozzle 124 located at the center 125 of the downstream side 123 of the substrate structure 120. The nozzle 124 directs the water flow outwardly from the center 125 to avoid stagnant water flow at the center 125 of the substrate 120, which potentially can cause a hotspot in the center 125 of the substrate 120. Thus, the nozzle 124 facilitates more uniform temperature distribution on the beam (or upstream) side of the neutron-generating target 100 (and 102, 103 and 104). The nozzle is further configured to provide a minimum pressure drop for the inlet water, thus directing the water flow from one direction to another, i.e., rotating it by 90°, and minimizing the resistance on the water flow. The size of the nozzle as well as its geometry is optimized to maintain the turbulent regime of the flow and at the same time to avoid stagnant eddies. The nozzle 124 is one of conically shaped or semi-spherically shaped.

As depicted in FIG. 4, the plurality of channels 122 is shown to include four (4) channels 122A, 122B, 122C and 122D extending from a position proximate the nozzle 124 at the center 125 of the substrate structure 120 towards the periphery of the substrate structure 120. The plurality of channels 122 form a configuration of parallel spiral windings to evenly distribute cooling across a maximum area of the substrate structure.

Figure 8:
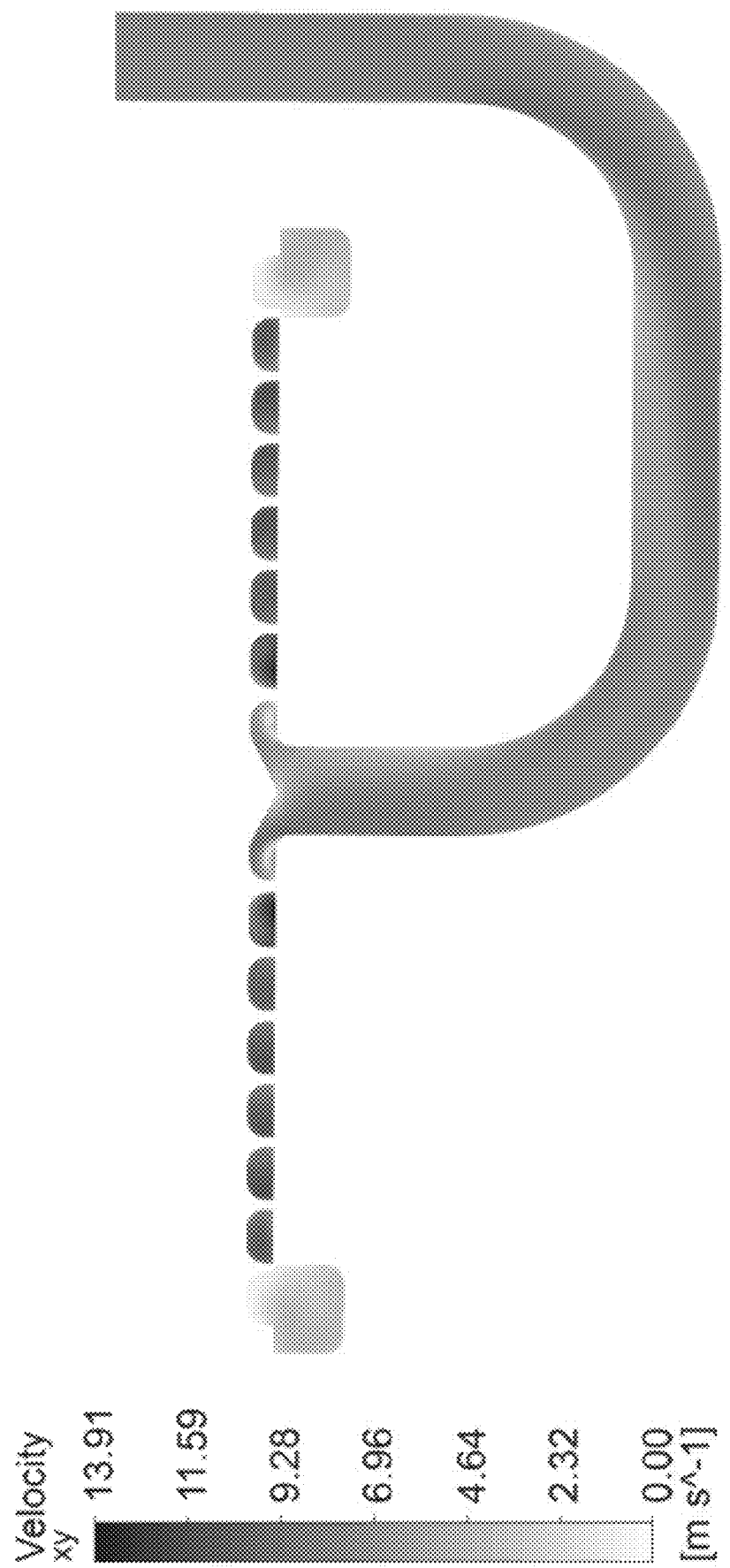
FIG. 8 is an image depicting the results of a simulation of operation of an embodiment of the target.

The results of a simulation of target operation are shown in FIG. 8. The target 100 is enclosed in a water-cooled fixture. As a proton beam bombards the target surface from the beam side (upstream side), the protons interact with the target 100 and slow down inside the target material (lithium layer 110 and substrate 120), and thus heat up the target 120. The water inlet flow is connected to the center 125 of the target substrate 120, to the nozzle 124, which directs the flow of water outwardly from the center 125 towards the periphery of the target substrate 120. The water passes through the water channels 122, removing the heat from center 125 to the periphery 126 of the target 120. Two water outlet channels do symmetrize the flow and make it more uniform. The results of the simulation of the water flow are shown onside the water channels for the uniform heat flux of 3.5 $MW/m^2$, which correspond to total beam power of 25 kW distributed on the target surface of 100 millimeters (mm) in diameter. The calculations show that for generating of the $10^{13}$ n/s (the source strength which is needed for a commercial application) the power density of 3.5 $MW/m^2$ is the highest possible for this type of the target.

Figure 9:
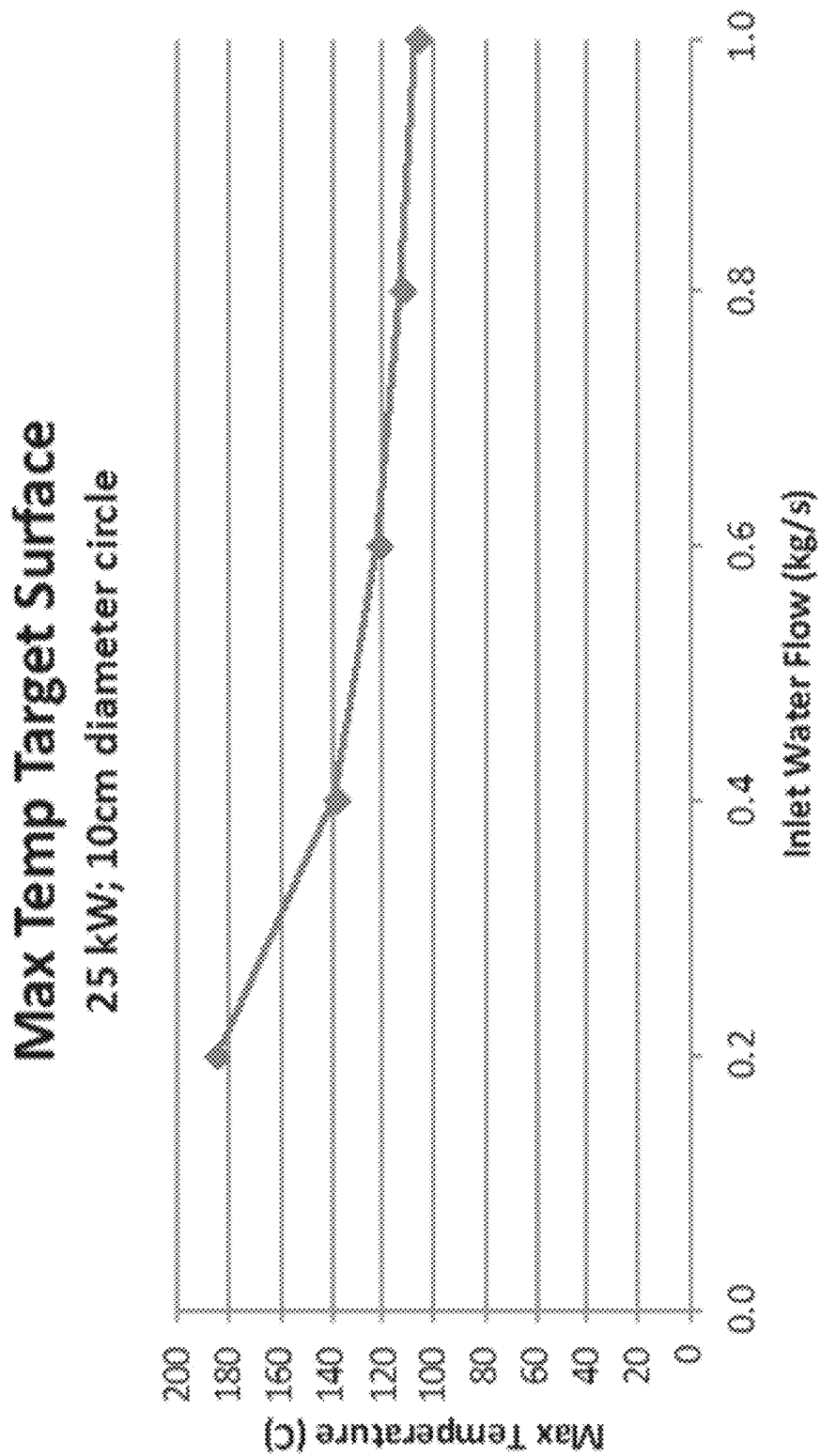
FIG. 9 is a graph depicting the results of a simulation of maximum target temperature (on the beam side of the target) versus inlet water flow into the support structure of an embodiment of the target.

The results of the simulation of maximum target temperature (on the beam side) versus inlet water flow are shown in the FIG. 9. The depicted results show that the water flow is an important parameter for the cooling of the target. Since the lithium melting point is only about 180° C., a relatively high water flow rate is needed for cooling down the surface of the target. If some necessary margin is taken into account, then an inlet flow rate of more than 0.6 kg/s tends to appear to be sufficient.

Figure 10:
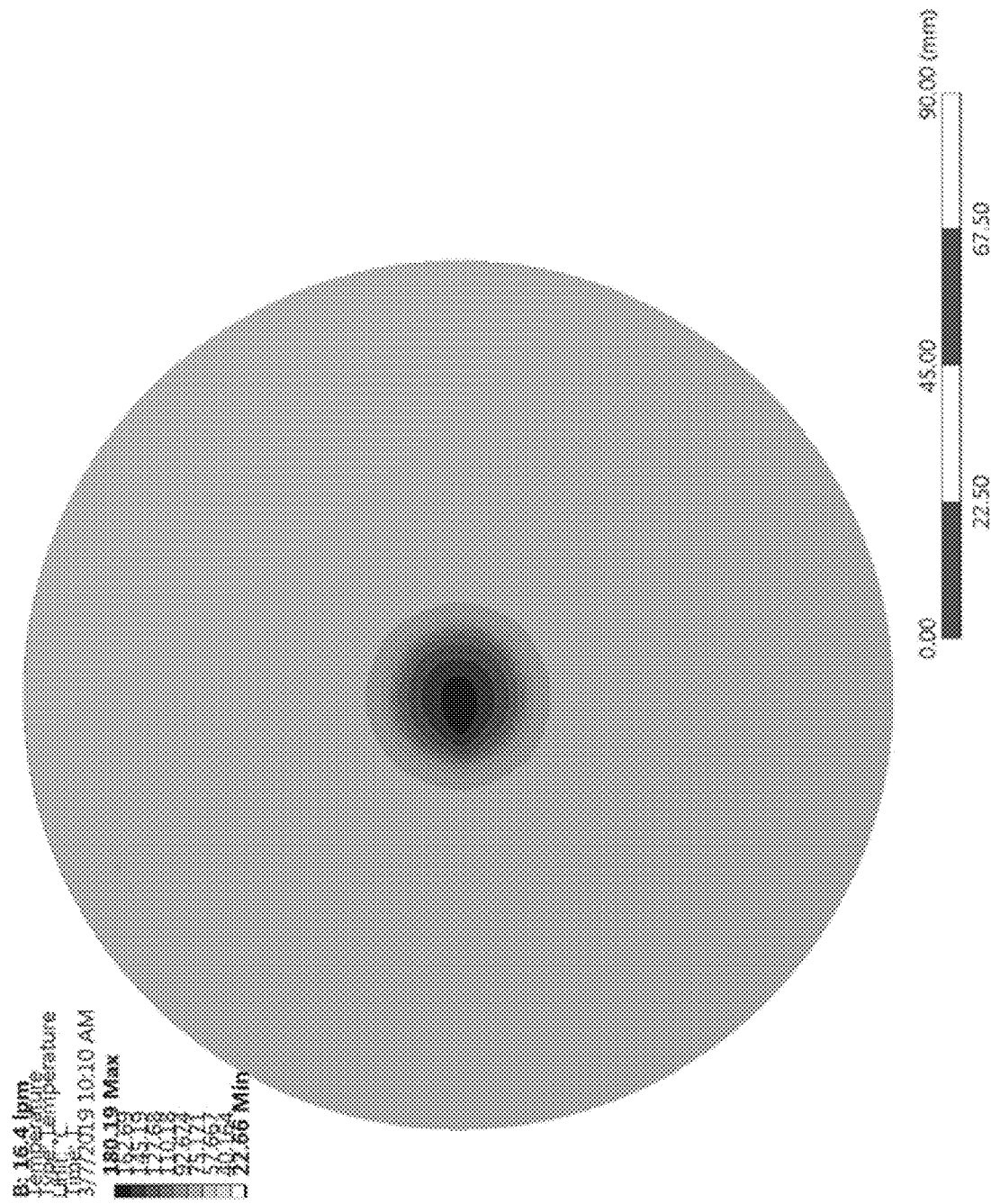
FIG. 10 is an image depicting the thermal test results of an embodiment of the target.

FIG. 10 shows the thermal tests results of an example embodiment of the neutron-generating target presented herein. The target was heated with a proton beam of 3.8 kW total energy and the beam was applied into a 24 mm diameter channel, which corresponds to a power density of 8.8 MW/m2 (almost three-fold relatively to maximum power density needed). The water parameters includes: inlet pressure of 39 pounds per square inch (psi), outlet pressure of 32 psi, water flow of 16 lpm, and water inlet temperature of 23° C. The temperature profile of the target ranged from a temperature of about 23.3° C. over a substantial portion of the target from the periphery toward the center to a temperature of about 180.81° C.

For the lithium layer 110 of the target 100 to remain in a solid state under normal operation conditions, requires the heat removal configuration of the neutron-generating target 100 to be highly effective. The simulation results suggest this to be the case for the heat removal configuration of the subject neutron-generating target 100. Maintaining the lithium in a solid state is a great advantage because: a) liquid lithium is a highly corrosive material that can destroy the heat removal support structure 120; and b) the evaporation rate of liquid lithium is much higher than solid lithium and the resulting evaporation and/or sputtering of target material (including radioactive 7Be) presents a serious operational problem.

Various aspects of the present subject matter are set forth below, in review of, and/or in supplementation to, the embodiments described thus far, with the emphasis here being on the interrelation and interchangeability of the following embodiments. In other words, an emphasis is on the fact that each feature of the embodiments can be combined with each and every other feature unless explicitly stated otherwise or logically implausible.

According to embodiments, a neutron beam system comprises an ion beam injector, a high voltage (HV) tandem accelerator coupled to the ion beam injector, and a high-energy beamline extending from the tandem accelerator to a neutron target assembly housing a neutron-producing target, the neutron-producing target including a thin film of neutron generating material mounted onto a heat-removal support structure configured to accommodate an extremely high heat flux.

According to embodiments, a neutron-producing target comprises a heat-removal support structure, and a layer of neutron generating material mounted onto the support structure, the support structure being configured to accommodate an extremely high heat flux.

In embodiments, the neutron generating material comprises lithium.

In embodiments, the heat-removal support structure is directly cooled with a liquid coolant.

In embodiments, the heat-removal support structure is configured to accommodate a heat flux of up to about 3-4 MW/m^2.

In embodiments, the neutron target assembly housing having a liquid coolant inlet directing a flow of coolant towards the heat-removal support structure.

In embodiments, the heat-removal support structure is configured to maintain the turbulent flow regime for the liquid coolant.

In embodiments, the heat-removal support structure is configured to distribute the flow of liquid coolant directed at a center of the heat-removal support structure toward a periphery of the support structure via a plurality of channels formed in a surface of the heat-removal support structure.

In embodiments, the plurality of channels includes n channels where n is an even number or equal to 2 or more.

In embodiments, the plurality of channels form a configuration of parallel spiral windings to evenly distribute cooling across a maximum area of the surface of the heat-removal support structure.

In embodiments, the neutron beam system further comprises a nozzle located at a center of a surface of the heat-removal support structure.

In embodiments, the nozzle directs the flow of coolant outwardly from the center of the heat-removal support structure to avoid stagnant water flow at the center of the support structure.

In embodiments, the nozzle is configured to cause a minimum pressure drop for the inlet coolant.

In embodiments, the nozzle is configured to direct the flow of coolant from a first direction to a second direction orthogonal to the first direction.

In embodiments, the nozzle is configured to maintain the turbulent regime of the flow of coolant.

In embodiments, the size and geometry of the nozzle is optimized to maintain the turbulent regime of the flow of coolant.

In embodiments, the nozzle is one of conical shape or semi-spherical shape.

In embodiments, the heat-removal support structure is made of material having a high thermal conductivity.

In embodiments, the material having a high thermal conductivity is one of copper, copper-diamond powder composites or CVD diamond.

In embodiments, the neutron generating target further comprises an interlayer interposing the neutron producing film and the heat-removal support structure.

In embodiments, the interlayer comprises a material with high solubility for Hydrogen and/or with a high diffusion coefficient for Hydrogen.

In embodiments, the interlayer comprises one of pure Ta, Ti, Pd, Nb, V, Ni, or alloys of thereof with themselves or/and with copper.

In embodiments, the neutron generating target further comprises a protective layer positioned on top of the neutron producing film layer.

In embodiments, the protective layer is positioned in a manner that the protective layer covers all of the neutron producing film evenly at the top and on the sides of the neutron producing film.

It should be noted that all features, elements, components, functions, and steps described with respect to any embodiment provided herein are intended to be freely combinable and substitutable with those from any other embodiment. If a certain feature, element, component, function, or step is described with respect to only one embodiment, then it should be understood that that feature, element, component, function, or step can be used with every other embodiment described herein unless explicitly stated otherwise. This paragraph therefore serves as antecedent basis and written support for the introduction of claims, at any time, that combine features, elements, components, functions, and steps from different embodiments, or that substitute features, elements, components, functions, and steps from one embodiment with those of another, even if the following description does not explicitly state, in a particular instance, that such combinations or substitutions are possible. It is explicitly acknowledged that express recitation of every possible combination and substitution is overly burdensome, especially given that the permissibility of each and every such combination and substitution will be readily recognized by those of ordinary skill in the art.

To the extent the embodiments disclosed herein include or operate in association with memory, storage, and/or computer readable media, then that memory, storage, and/or computer readable media are non-transitory. Accordingly, to the extent that memory, storage, and/or computer readable media are covered by one or more claims, then that memory, storage, and/or computer readable media is only non-transitory.

As used herein and in the appended claims, the singular forms "a," "an," and "the" include plural referents unless the context clearly dictates otherwise.

While the embodiments are susceptible to various modifications and alternative forms, specific examples thereof have been shown in the drawings and are herein described in detail. It should be understood, however, that these embodiments are not to be limited to the particular form disclosed, but to the contrary, these embodiments are to cover all modifications, equivalents, and alternatives falling within the spirit of the disclosure. Furthermore, any features, functions, steps, or elements of the embodiments may be recited in or added to the claims, as well as negative limitations that define the inventive scope of the claims by features, functions, steps, or elements that are not within that scope.

What is claimed is:

1. A neutron beam system comprising:
   a beamline;
   a cap secured to the beamline, the cap comprising a cooling inlet at a center of the cap and a plurality of cooling outlets at a periphery of the cap; and
   a target enclosed by the cap and the beamline, wherein the target comprises a support structure, a neutron generating layer on a side of the target facing the beamline, and a conical or spherical nozzle protruding from a center of the support structure facing the cooling inlet of the cap and configured to direct a flow of coolant from the cooling inlet outwardly through a plurality of cooling channels extending along the support structure to the plurality of cooling outlets, wherein a terminus of the conical or spherical nozzle is flush with outlet ends of the plurality of cooling channels.

2. The neutron beam system of claim 1, further comprising:
   an ion beam injector; and
   a tandem accelerator coupled to the ion beam injector and the beamline, the tandem accelerator configured to accelerate an ion beam from the ion beam injector to the beamline.

3. The neutron beam system of claim 1, wherein the target is enclosed by the cap and beamline such that a vacuum seal is present between the target and an interior volume of the beamline, and a water seal is present between the target and the cap.

4. The neutron beam system of claim 1, wherein the neutron generating layer comprises lithium.

5. The neutron beam system of claim 1, wherein the plurality of channels form a configuration of parallel spiral windings.

6. The neutron beam system of claim 1, wherein the cooling inlet is configured to direct coolant in a downstream to upstream direction with respect to a beam axis, and the plurality of cooling outlets are configured to direct coolant in an upstream to downstream direction with respect to the beam axis.

7. The neutron beam system of claim 1, wherein the target further comprises an interlayer interposing the neutron generating layer and the support structure.

8. The neutron beam system of claim 7, wherein the interlayer comprises one of pure Ta, Ti, Pd, Nb, V, Ni, or alloys of thereof with themselves or/and with copper.

9. The neutron beam system of claim 1, further comprising a protective layer positioned over a side of the neutron generating layer facing the beamline.

10. The neutron beam system of claim 1, wherein each cooling channel of the plurality of cooling channels follows a curved path along the support structure, and wherein a channel surface of each cooling channel comprises a curved transition between a bottom of the channel surface and a side of the channel surface.

* * * * *